US010406303B2

(12) United States Patent
Anandhakrishnan

(10) Patent No.: US 10,406,303 B2
(45) Date of Patent: Sep. 10, 2019

(54) INTELLIGENT INHALER HOLSTER WITH A SYSTEM AND METHOD TO SENSE, TRACK PROPERTIES OF INHALED AIR AND MEDICATION, ALERT IN HOSTILE ENVIRONMENTS, MAP MEDICATION WITH PERSONAL DYNAMICS, INHALED AIR AND ENVIRONMENT FOR BETTER HEALTH

(71) Applicant: Vaidyanathan Anandhakrishnan, Bangalore (IN)

(72) Inventor: Vaidyanathan Anandhakrishnan, Bangalore (IN)

( * ) Notice: Subject to any disclaimer, the term of this patent is extended or adjusted under 35 U.S.C. 154(b) by 458 days.

(21) Appl. No.: 14/725,931

(22) Filed: May 29, 2015

(65) Prior Publication Data

US 2015/0335834 A1 Nov. 26, 2015

Related U.S. Application Data

(63) Continuation-in-part of application No. 14/130,680, filed as application No. PCT/IB2013/060295 on Nov. 21, 2013.

(30) Foreign Application Priority Data

Sep. 25, 2013 (IN) .......................... 4346/CHE/2013
Feb. 4, 2015 (IN) ............................. 561/CHE/2015

(51) Int. Cl.
*G06N 7/00* (2006.01)
*A61M 15/00* (2006.01)
(Continued)

(52) U.S. Cl.
CPC ........ *A61M 15/0066* (2014.02); *A61M 15/00* (2013.01); *A61M 15/008* (2014.02);
(Continued)

(58) Field of Classification Search
None
See application file for complete search history.

(56) References Cited

U.S. PATENT DOCUMENTS

| 7,594,889 B2 * | 9/2009 | St. Ores | ............... | A61B 5/0031 |
| | | | | 600/301 |
| 8,807,131 B1 | 8/2014 | Tunnell | | |
| 2009/0194104 A1 | 8/2009 | VanSickle | | |

OTHER PUBLICATIONS

Krause, A. et al. "Context-Aware Mobile Computing: Learning Context—Dependent Personal Preferences From a Wearable Sensor Array," IEEE Transactions on Mobile Computing, vol. 5. No. 2. XP001545959, Feb. 1, 2006, pp. 1-15.

(Continued)

*Primary Examiner* — Wilbert L Starks
(74) *Attorney, Agent, or Firm* — J. Peter Paredes; Rosenbaum IP, P.C.

(57) ABSTRACT

The invention discloses an intelligent inhaler holster with a system and method to sense, track properties of inhaled air and medication, alert in hostile environments, map medication with personal dynamics, inhaled air and environment for better health, along with predictive and prognostic analytics. The system includes a sensor module to sense various environmental parameters of the personal environment envelope surrounding the individual. The system also includes an inhaler module configured to track the medication taken by the user. The system also has a processing module to collect data from multiple numbers of environmental sensors and further dynamically processes the information from the inhaler module including the time and location from where the user has taken medication. The processing module alerts for deviations, learns the preferred settings, advises based on trends, predictive and prognostic analytics.

9 Claims, 8 Drawing Sheets

(51) Int. Cl.
*A61M 16/00* (2006.01)
*G06F 19/00* (2018.01)
*A61M 16/16* (2006.01)

(52) U.S. Cl.
CPC ...... *A61M 15/009* (2013.01); *A61M 15/0083* (2014.02); *A61M 16/0051* (2013.01); *A61M 16/021* (2017.08); *G06F 19/3462* (2013.01); *A61M 15/0045* (2013.01); *A61M 15/0085* (2013.01); *A61M 16/161* (2014.02); *A61M 2016/0027* (2013.01); *A61M 2205/3303* (2013.01); *A61M 2205/3358* (2013.01); *A61M 2205/3368* (2013.01); *A61M 2205/3375* (2013.01); *A61M 2205/3553* (2013.01); *A61M 2205/3592* (2013.01); *A61M 2205/502* (2013.01); *A61M 2205/52* (2013.01); *A61M 2205/583* (2013.01); *A61M 2205/8206* (2013.01); *A61M 2230/432* (2013.01); *A61M 2230/50* (2013.01); *A61M 2230/63* (2013.01); *G06N 7/00* (2013.01)

(56) References Cited

OTHER PUBLICATIONS

Satish, U. et al. "Is CO2 an indoor Pollutant? Direct Effects of Low-to-Moderate CO2 Concentrations on Human Decision-Making Performance," Environmental Health Perspectives, vol. 120, No. 12, Dec. 2012, pp. 1671-1677.

\* cited by examiner

INTELLIGENT INHALER HOLSTER WITH A SYSTEM AND METHOD TO SENSE, TRACK PROPERTIES OF INHALED AIR AND MEDICATION, ALERT IN HOSTILE ENVIRONMENTS, MAP MEDICATION WITH PERSONAL DYNAMICS, INHALED AIR AND ENVIRONMENT FOR BETTER HEALTH

The following specification particularly describes the invention and the manner in which it is to be performed:

TECHNICAL FIELD OF THE INVENTION

The present disclosure relates to smart inhaler with environmental tracking, monitoring and enable control of the personal environment. More particularly, the present disclosure relates to a system and method for continuously recording the various environmental parameters both around an individual (effectively the inhaled air), as well as the outside weather properties along with location and time, thus mapping the entire context of an 'individual-time-inhaled air properties-outside air properties' along with details pertaining to medication, and enabling alerts or warning regarding vulnerability of a user to a location, missed dosage of medication, through a user interface, store such data in the cloud, to provide predictive and prognostic diagnostics.

BACKGROUND OF THE INVENTION

Breathing is an involuntary act that keeps a person alive. Human beings, as they evolved, used to co-exist with nature/environment. The quality of air one breaths depends up on the place the person inhabits. Historically, human beings breathed healthy fresh air, as they used to co-exist with environment. Industrialization and urbanization has changed it substantially. Recorded history of industrialization has shown soot spewing chimneys, hazardous work environment that the workers had to contend with. Further advancement of technologies provided for controlled environment through various equipments such as air-conditioning devices that performed different functions such as cooling and heating of air, humidifying and dehumidifying air as required, enabling conditioned working and living environments. Concurrently, new technologies in building sciences, advancement in materials and rapid urbanization have allowed raise/create buildings that are air tight and provide nearly full control over the environment inside the premises. Over the time, more and more houses have got air conditioned, thus having controlled indoor environment. In industrialized and developed countries, people move from conditioned environment in the house to a work place or school or any other public place that is conditioned through an air conditioned car or bus or any other public transport system. In developing countries such as China, India, such practices are growing and the lifestyle is becoming universal. In effect, people live in a controlled environment by choice or by default. When one says indoor, one refers to such environment of staying indoor in a controlled environment. While there is a perception that indoor air is clean and healthy, recent studies have highlighted the problems by calling them Indoor Air Pollution.

Respiratory illness due to pollution is a major subject of discussion. As the wordings suggest, the respiratory illnesses are caused primarily by the quality of air that one inhales. When one refers to Air, there is an implicit understanding that there are no undesirable elements such as pollution in the air. While healthy clean fresh air is essential for a healthy being, it is the pollution that is a culprit in impacting people/individuals. In the US, various institutions including Environment Protection Agency (EPA), Lawrence Berkeley National Laboratory (LBNL) have done enormous amount of research on indoor air pollution. Rapid industrialization, transportation, building industry has caused outside air to be one of the most polluted. The indoor air and outdoor air pollutants could be physical particles and matter such as dust, dander, carpet fibers/fibres and fibroids, or chemicals such as Carbon Monoxide, Carbon di-Oxide, Sulphur Di Oxide, Nitrogen Di Oxide, Ozone or biological particles such as pollen, seeds etc., or could be particulate matter (PM) of various sizes in microns PM10, PM2.5 and PM1.0. The health impacts of these have been extensively documented by WHO/EPA/CDC and other internationally recognized institutions. As a result of these various initiatives have been drawn to create public awareness for both Indoor air Pollution as well as Outdoor Air Pollution. The Indoor Air pollution initiatives typically come under Indoor Air Quality (IAQ) improvement. As regards Outdoor air there are Government initiated steps to sensitize people through Air Quality Index (AQI). This AQI is a One Color, One Number to sensitize people to know the extent of quality of air through different colors—Green, Light Green, Amber, Mauve, Red, Blood Red showing different levels of pollution. The color schema and the number schema vary from country to country. These colors are given for illustrative purpose. Such initiatives are for sensitizing the people to stay alert on the impact of pollution, take required regulatory steps to reduce the extent of pollution, take required precautionary measures individually The number of individuals globally affected by respiratory illness is a staggering more than 500 mn individuals according to WHO. It is estimated that over 4 Mn die every year due to Acute Respiratory illness. The respiratory illness comes in various forms Common Cold, Asthma, COPD, Sinusitis, Bronchitis and other forms. In the US alone it is estimated that there are more than 53 mn individuals (young, old, children) who are impacted by various forms of respiratory illnesses such as asthma, sinusitis.

Respiratory illness as the name suggests is invariably due to the inhaled air or more specifically, the pollutants, as stated earlier. While the cause and effect of which pollutant may cause which specific human body reaction might not have been exactly established, there is increasing understanding of this. Once with a respiratory illness, naturally one looks for a curative medicine. Doctors prescribe medication—that specifies the medicine, dosage, frequency etc. As regards the cause and effect relationship, the doctors quite often assess the reason as "pollution in the air." The medication varies from general pills/tablets, to syrups and in cases requiring specific higher care, medicine inhalation through inhalers is prescribed.

Inhaled air varies depending upon place—indoor or outdoor, type of building, extent of exposure etc. In a natural building that has windows and doors relatively open, generally provide relief from the ambient environment. When outside is very hot, the inside temperatures will be lesser and vice versa, namely warmer inside when the ambient environment is very cold. However, the other chemical properties of outside air (ambient air) and inside tend to be similar. The indoor may be, very polluted or very clean depending upon the ambient environment. Now, however, the advancements in construction engineering and building sciences have made many of the buildings (offices and homes) nearly air tight. Newer practices of curtain walled glass (glass exterior) or insulated pre engineering boards or aluminum clad external finishes of buildings do not allow fresh air to infiltrate through the wall. In effect, the indoor environment is distinctly different and is controlled as designed and implemented by the occupants. Lack of fresh air has created various illnesses and World Health Organization (WHO) in their studies categorized such phenomenon as 'Sick Building Syndrome'—SBS. The resultant poor 'Indoor Air Quality' called IAQ has been a subject of serious discussion and debate in the industry and amongst people.

The likelihood of immediate reactions to indoor air pollutants depends on several factors. Age and preexisting medical conditions are two important influences. In other cases, whether a person reacts to a pollutant depends on individual sensitivity, which varies tremendously from person to person. Some people can become sensitized to biological pollutants after repeated exposures, and it appears that some people can become sensitized to chemical pollutants as well.

Certain immediate effects are similar to those from colds or other viral diseases, so it is often difficult to determine if the symptoms are a result of exposure to indoor air pollution. For this reason, it is important to pay attention to the time and place symptoms occur. If the symptoms fade or go away when a person is away from home, for example, an effort should be made to identify indoor air sources that may be possible causes. Some effects may be made worse by an inadequate supply of fresh/outdoor air or from the heating, cooling, or humidity conditions prevalent in the home. Other health effects may show up either years after exposure has occurred or only after long or repeated periods of exposure. These effects, which include some respiratory diseases, heart disease, and cancer, can be severely debilitating or fatal. It is prudent to try to improve the indoor air quality in your home or office even if symptoms are not noticeable.

While pollutants commonly found in indoor air are responsible for many harmful effects, there is considerable uncertainty about what concentrations or periods of exposure are necessary to produce specific health problems. People also react very differently to exposure to indoor air pollutants. Further research is needed to better understand which health effects occur after exposure to the average pollutant concentrations found in homes and which occurs from the higher concentrations that occur for short periods of time.

Quite often $CO_2$ is taken as a proxy for the indoor pollution. Recent studies have increased the importance of understanding the $CO_2$ levels in the room. A recent Study conducted by Dr. Usha Satish, Dr. Mark J Mendell et. al on behalf of National Institutes of Health, US Department of Health and Human Sciences titled "Is $CO_2$ an Indoor Pollutant? Direct Effects of Low-to-Moderate $CO_2$ Concentrations on Human Decision-Making Performance" has found statistically significant decrements in decision making performance.

It is also known that for respiratory illnesses such as asthma the air that one breathes is of extreme relevance. Quite often a person who chokes/gasps for breath rushes outside or changes the location to get a whiff of fresh air. It is known that high $CO_2$ levels increase discomfort for asthma patients. Similarly, it is known that relative humidity of air influences the comfort for asthma patients. Over time and experience a patient learns on the environment where the person is comfortable and would prefer such environment as compared to another environment that the person knows as discomforting. It is also reported that the absenteeism in schools is because of the quality of the indoor air.

A lot of contemporary research is going on the need to have lower levels of $CO_2$ in the class room so that the children breathe better quality of air.

Epidemiology is the cornerstone of public health and equips policy decisions by the Government agencies; the study helps identifying the risk factors for a disease and helps in preventive steps for occurrence of such disease/illness. Every person keeps a record of the illness to enable better medical history and treatment for longevity and quality of life. In these days of advanced technology, medical records and genetic history/genealogy analysis is undertaken to arrive at causes for the illness or as important factors for the specific treatment that would be provided to the person. While such level of information is gathered, seldom does a person have a record of the air that he breathed. This collection of data of the individual, the quality of air that he breathed along with the backend analysis of the data collected from several (millions) of individuals would well provide the background data for Epidemiologists to analyze the data that will help formulate health policies. While several factors are important for health, lifestyle or occurrence of an illness, such collected data in conjunction with the ambient weather data, type of activities undertaken by the person would provide enormous insight for the Epidemiologists.

In as far as the equipments such as air conditioners that provide controlled indoor environments for the space are concerned; they are capable of providing the preferred environment. However, the type of setting of such equipments/machines is not a dynamic depending upon the person's requirement, but they are a static based on specific set points such as temperature, relative humidity. As regards Carbon Di oxide levels, these would enable fresh air damper opening based on such set points. In some of the more advanced equipments there are a set of programmed set points or patterns based on which these equipments operate. In a few of the newer control devices, the equipments learn based on the settings and patterns of usage specifically with regard to temperature. However, none of these devices provide a dynamically variable preferred setting based on the persons' preferred setting that correlates to his health. As an example, if an asthmatic person would prefer an air envelope of say Temperature of 23 to 27 deg. C. with a relative humidity of 50% to 65% and a CO2 level of lesser than 600 ppm in the room, the equipment in his house could be told to provide such environment as much as his office equipment or any other place that he would visit. Thus, there is an indispensable link between the air pollution and the dosage of medication for the asthmatic patients.

There are many existing patent application which talk about the smart inhalers. The U.S. Pat. No. 8,807,131 (B1) discloses devices and methods for monitoring a patient's compliance with an asthma inhaler treatment regimen. It is disclosed that the device may be incorporated with a smart phone to provide alerts and notification generated as a result of monitoring of various parameter including the environmental parameters when the patient is taking the inhaler. The device has a predictive indicator for how like patients may respond to similar environments, treatment regimens, and what may trigger attacks in specific patients. But here, the device is not considering the personal environment of the user instead using the generic environmental characteristics. Even though while it appears to capture the patient's environmental parameters, this does not capture environmental parameters continuously. There would be lag between a person inhaling air and its pollutants and the patient's body reacting to such inhaled pollution, so without continuous analysis of inhaled air it is difficult to give accurate predictions. Thus, the prediction may not be that accurate as when the personal environment is tracked continuously for a user. The data collected would not be adequate to evolve a cause and effect relationship. In absence of such data, prognostic predication would not be possible.

The United States patent application no: US2009194104 (A1) discloses a device and method to monitor, track, map, and analyze usage of metered-dose inhalers in real-time. This invention helps in recording the time, date and location, where a medication is used accurately and reliably, and also for transmitting, collecting, and using that data to improve clinical care, disease management, and public health surveillance. This invention doesn't provide a prognostic prediction for the user.

There are many products already in market as smart inhalers such as Smartinhaler™ from Nexus 6, Propeller from Propeller Health, Inspiromatic™ from Inspiro medical and Airsonea™ from Airsonea. Among these there are few products, which provide alert when there is missed dosage or when a person is in a new zone where some other person needed an extra dosage previously then the product gives an alert regarding this. But none of these products provides a predictive and prognostic diagnostics to warn patients in advance about vulnerabilities in new places—whenever they travel. And also to enable effective research with the appropriate data for Doctor on various categories of patients and to assess probabilities of pre-asthmatic.

Thus, there is a need for an intelligent user friendly inhaler that would help patients, to alert them in hostile environments, guide them to learn about their preferred health environment, that would enable the patient to optically medicate (no under dosage or over dosage) live a healthy life by a Smart inhaler system that auto learns, heuristically and through algorithms that captures the micro environment/personal cloud of the air that the individual would seek, preferred settings the personal preferences, dosage of medication, alert in event of deviations from the preferred settings or any change from the expected medication, provide data to the backend that could through a period of time of accumulated data provide valuable health insights to the person as well as act as the database of several individuals health records to enable Health Specialists, Epidemiologists to study and analyze such data to guide the patients who uses the intelligent inhaler.

SUMMARY OF THE INVENTION

The present invention overcomes the shortcomings in the existing prior arts by providing an a intelligent inhaler system that would capture the micro environment/personal cloud of the air that the individual would seek, preferred settings the personal preferences, dosage of medication, alert in event of deviations from the preferred settings or any change from the expected medication, provide data to the backend that could through a period of time of accumulated data.

According to an embodiment, the invention discloses intelligent inhaler holster system to sense, track properties of inhaled air and medication of an individual. The system includes a sensor module comprising at least one of a plurality of environmental sensors configured to sense a plurality of environmental parameters of a personal environment envelope surrounding the individual and a plurality of biological sensors to sense a plurality of biological and physiological condition of the individual. These sensors continuously sense the plurality of environmental parameters to track the properties of inhaled air. The system further includes an inhaler module comprising a dosage counter. The dosage counter counts the number of dosages available in the inhaler. The inhaler module also tracks the medication taken by the user and details of the medication. The system includes a personal environment envelop setting module configured to define preferred settings based on input from the individual through a user interface. The input from the individual includes information not limited to the environmental preference, medication details. The personal environment envelop setting module also machine learn individual's preference of the personal environmental envelope and dosage of the medication with respect to the inhaled air and automatically generate the preferred settings for the individual based on the learning. The system also has a processing module configured to collect data from plurality of environmental sensors regarding ambient environmental conditions with reference to the geographical location of the individual and to collect data from plurality of external sources regarding ambient environmental conditions with reference to the geographical location of the individual and the personal environmental envelope. The processing module further collects data from the inhaler module regarding the dosage, time at which dosage is taken to dynamically process the preferred personal environment data vis-à-vis the ambient environmental conditions and the medication details. The processing module is further configured to process at least one of the plurality of environmental parameters sensed by the plurality of environmental sensors, the sensed biological and physiological condition of the individual, the medication details from the inhaler module and the preferred settings to generate one or more alerts, wherein the alert indicates a deviation of at least one environmental parameter from a corresponding preferred setting or deviation from expected medication. The system also has a server module configured to receive, store, analyze and machine learn from data of the plurality of environmental parameters and biological and physiological condition, sensed by the environmental sensors and biological sensors from the sensor module and the preferred settings along with ambient environmental data from plurality of individuals for epidemiology study. The system generates alerts in hostile environments, map medication with personal dynamics, inhaled air and environment for better health.

According to another embodiment, the system further comprises a communication module to receive and transmit data between various modules and to communicate alerts and interface with plurality of user devices and environment setting equipments. The personal environment envelop setting module is further configured to interact and interface with plurality of environment setting equipments to achieve the preferred setting for the individual based on the medication details. The inhaler module further comprises an inhaler setting module to set the timing and dosage of the inhaler medication for the individual.

According to another embodiment, the invention discloses a method for recording personal environment and to enable preferred personal indoor environment. The method includes step of collecting data regarding environmental parameters of the personal environment envelope surrounding an individual and biological and physiological conditions of the individual from a plurality of sensors. The method also includes the step of collecting data from the inhaler module, where in the data includes medication details, dosage taken and time. The method also has the step of receiving input from the individual regarding preferred personal environment setting and the dosage requirement of the medication through a user interface and processing the collected data and received input to identify any variations in the preferred personal environment settings to generate one or more alerts, wherein the alert indicates a deviation of at least one environmental parameter from a corresponding preferred setting or deviation from an expected medication.

According to another embodiment, the method further includes the step of communicating the alerts and interface with plurality of user devices and equipments. The step of collecting data further has data of the individual's biological and physiological conditions from the sensors implanted in the body or worn on the body. The further includes the step of recording the various inputs received from the individual, the inhaler and the sensors.

Thus, the system and method disclosed would capture the micro environment/personal cloud of the air that the individual would seek, to alert the user on missed dosage. The invention provides reminder as audio alerts and visual alerts on dosage to be taken. The present invention further helps the user to be conscious of locations of frequent inhalations and also to supervise the asthmatic patients. The present invention may warn patients in advance about vulnerability of places.

BRIEF DESCRIPTION OF THE DRAWINGS

The foregoing and other features of embodiments will become more apparent from the following detailed description of embodiments when read in conjunction with the accompanying drawings. Elements in the figures have not necessarily been drawn to scale in order to enhance their clarity and improve understanding of these various elements and embodiments of the invention. Furthermore, elements that are known to be common and well understood to those in the industry are not depicted in order to provide a clear view of the various embodiments of the invention. Thus, in the interest of clarity and conciseness, the drawings are generalized in form, wherein.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable a person skilled in the art to practice the invention, and it is to be understood that other embodiments may be utilized and that logical, mechanical, and other changes may be made within the scope of the embodiments. The following detailed description is, therefore, not be taken as limiting the scope of the invention, but instead the invention is to be defined by the appended claims.

The invention discloses a system, method and inhaler holster to record continuously the personal environment and the location and time when the inhaler is used to identify the remaining dosage and to map the usage of inhaler with the personal environment.

Figure 1:
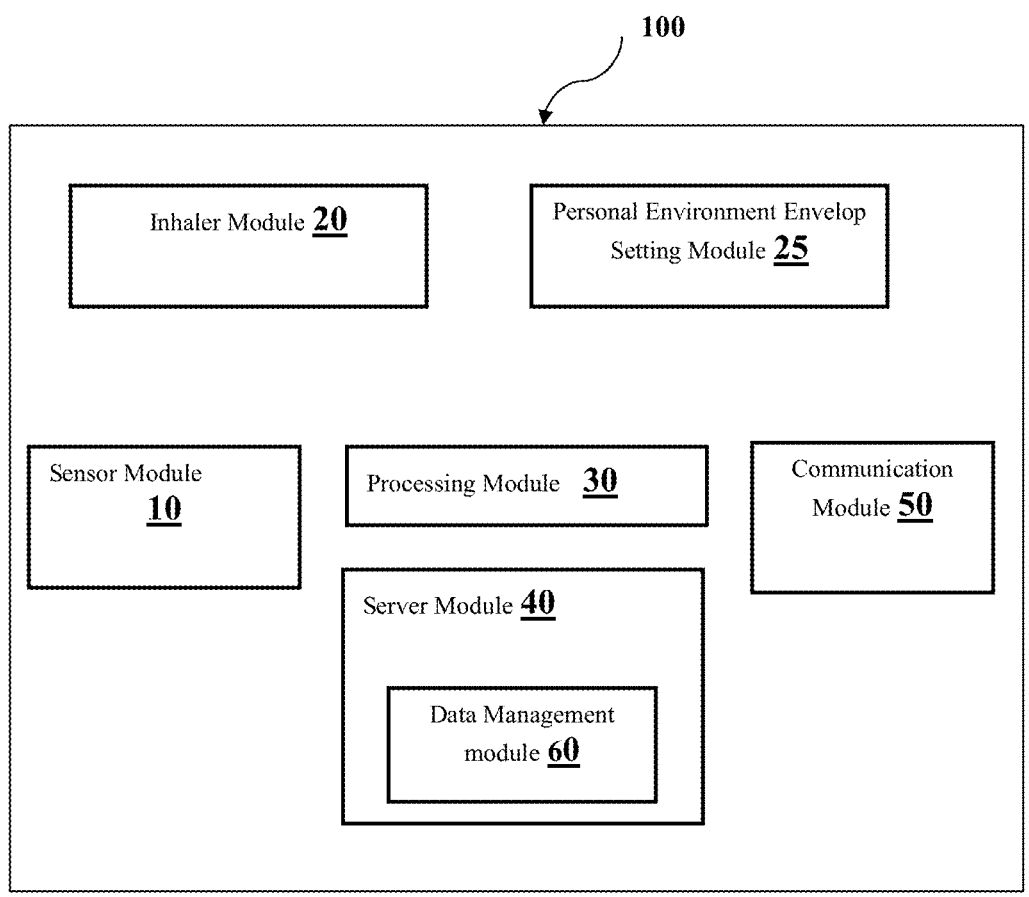
FIG. 1 illustrates the overall block diagram of the system, in accordance with an embodiment of the invention.

FIG. 1 illustrates the overall block diagram of the system in accordance with an embodiment of the invention. The system includes a sensor module 10 which has at least one of a plurality of environmental sensors configured to sense various environmental parameters of the personal environment envelope surrounding the individual and a number of biological sensors to sense a plurality of biological and physiological condition of the individual. In certain scenario the system may only have environmental sensors; in other scenarios it has the environmental sensors as well as the biological sensors. The environmental sensors described earlier includes sensors to collect environmental data such as $CO_x$ set of gases, $NO_x$ set of gases, SOx set of gases, volatile organic compounds, Radon, solid pollutants known as particulate matters of various sizes including but not restricted to dust, pollen, fine particles, Relative humidity (Rh), temperature, sound, light (harmful or beneficial), direction of flow of wind, location, direction in which the individual is facing or moving, altitude, barometric pressure, movement of the individual, alpha, beta and gamma wave etc. The biological sensors may be implanted in the individual's body or may be present on the body. The biological sensor includes sensors for identifying both the biological components as well as the physiological condition of the individual.

The system also includes an inhaler module comprising an inhaler holster that may be a holder/container/made of metal, polymer or any suitable material to hold a canister, medicine holder. For the purpose of this invention, reference to medicine could be any type of medicine, liquid, spray or a dry powder medicine as prescribed to the user by a Doctor or Hospital or any other authorities. The invention specifically is about the inhaler holster system, which may be a single or plurality of objects or units to communicate inter se either through wired or wireless protocols. The system also includes an inhaler module 20 configured to track the medication taken by the user. The inhaler module 20 tracks when and where the user has taken medication and also includes a dosage counter. The dosage counter counts the number of dosage available in the inhaler. The sensors for counting the dosage are fixed on the holster of the inhaler. Further, the inhaler module 20 stores the data regarding the expiry of the medicine, batch of the medicine and so on. The system further includes an inhaler setting module to set the timing and dosage in accordance with the inhalation routine of the user.

The system also has a personal environment envelop setting module 25 configured to define preferred settings based on the input from the individual through a user interface such as a mobile, tablet or a phablet. The easy to read infographics, interactive signs such as like it, do not like it visuals will enable user friendly screen. The input from the individual includes information includes at least one of the environmental preference or medication details. The personal environment envelop setting module 25 is also configured to machine learn independently or with server module 40 about the individual's preference for the personal environmental envelope and the details about medication to automatically generate the preferred settings for the individual based on the learning.

The system also has a processing module 30 to collect data from numerous environmental sensors regarding ambient environmental conditions with reference to a geographical location of the individual. The processing module 30 also collects data from plurality of external sources regarding ambient environmental conditions with reference to the geographical location of the individual and the personal environmental envelope. The processing module 30 further dynamically processes the information from the inhaler module 20 including the time and location from where the user has taken medication. The processing module 30 processes the sensor data so as to identify the environmental parameters that may have caused the need for medication especially if the dosage is not according to routine medication. If the processing module 30 identifies a deviation from the preferred settings in the environment or in the usage of medication then the processing module 30 generates alerts to the desired users. The desired user includes the one who uses receives the medication and their care takers including medical professionals. The alert generated by the processing module 30 includes alerts when the user misses routine dosage of medication. The system is also capable of learning from the user's history of usage of inhaler. The system may warn the user when the user is in a place and the place has a personal environment similar to an already known personal environment in which the user has taken dosage of medication through the inhaler. Thus the system helps in identifying the hostile condition of environmental parameters exists in an impending route. This helps the user either to avoid such places or take precautionary measures. The processing module 30 also generates the remainders for the medication based on the information regarding the dosage of medicine and the time schedule for the medicine.

According to an embodiment, the system further has a personal environment envelop setting module 25 is configured to interact and interface with various environment setting equipments to achieve the preferred setting for the individual. The various environment setting equipments include HVAC (heating ventilation and air conditioning), air conditioner, humidifier, air filtering equipments or actuators to enable flow of fresh air for diluting pollutants or any such equipment. The required communication protocols applicable is adhered to or followed through required software interfaces. In an exemplary scenario when the user is an asthmatic patient. If the user suddenly feels uncomfortable by entering into a new environment or in the existing environment itself. Then the user is provided with an option to ask the system to provide data that may have caused problem. The system is intelligent to identify the parameters which have varied from the previous values and intimate the user. Thus it may be helpful for the asthmatic patients or others who is very sensitive to various environmental factors to identify the same and include those parameters also in their preferred settings. The various environmental data, biological and physiological data and the user inputs are being stored in the system in order to facilitate a continuous learning for the system depending on many factors such as age and health of the user with respect to the environmental condition. The personal environment envelops setting module 25 enables the users to configure their settings. The personal environment envelop setting module includes the machine learning property which helps in identifying the preferred settings for the user.

The system also has a server module 40 configured to receive, store, analyze and machine learn from data of the plurality of environmental parameters sensed by the plurality of sensors from the sensor module and the preferred settings along with ambient environmental data and plurality of inputs received from different gadgets and sources for different uses and applications from plurality of persons for individual as well as collective studies including epidemiology study. The data stored by the server module 40 enables data mining for understanding the correlation of various environmental parameters on the individuals' health. The big data stored in the server may be used for health and epidemiology studies.

The system further has a communication module 50 to receive and transmit data between various modules and to communicate alerts and interface with plurality of user devices. The alerts and notifications are generated based on the user input received as well as the various environmental factors such as $CO_x$ level, $NO_x$, $SO_x$ level, humidity, temperature or any such environmental factors and the details of inhaler usage which may affect the individual. The personal environment envelope setting module utilizes the communication module 50 to communicate and interface with the environment setting equipments. The communication module 50 is configured to transmit the alerts or notifications to the various user devices which has been registered with the system to receive the alert. These user devices may be the mobile phone/tablets/phablets or any other device of the users who are authorized in receiving the individual's alert. The communication module 50 is further configured to transmit the user preferences from the personal environment envelop setting module 25 to the system so as to facilitate the setting of the preferred environment. The communication module 50 further enables the communication between the user device and the inhaler module 20 also. The processing module 30 receives the inhaler details and medication details from the inhaler module 20 with the help of communication module 50 where as the processing module 30 receives the data from the sensor module and from other external gadgets with the help of communication module. In certain scenario the communication module 50 transmits the control signals for various indoor environment control equipments such as air conditioners or other HVAC (heating ventilation and air conditioning) systems or AC based on the personal environment envelop setting module's input through the processing module 30. In this manner the personal environment envelop setting module interacts and interfaces with various environment setting equipments to achieve the preferred setting for the individual.

Figure 1A:
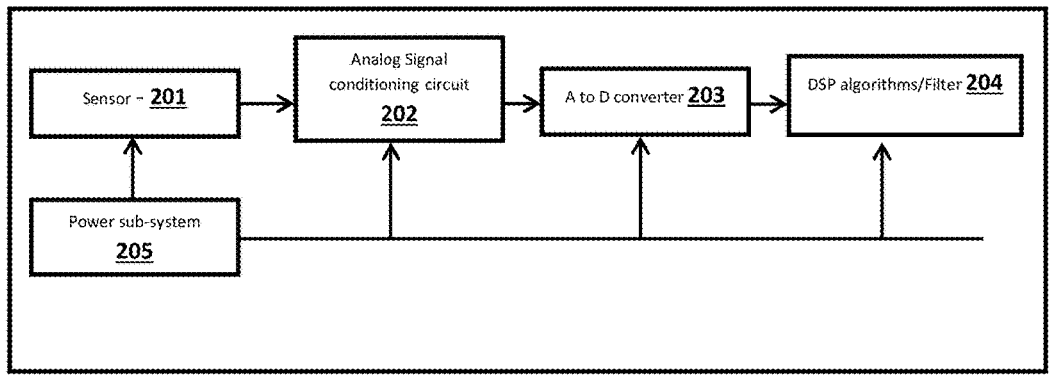
FIG. 1A illustrates the sensing module, in accordance with an embodiment of the invention.

FIG. 1A illustrates the sensor module 10 in accordance with an embodiment of the invention. The sensor/s 201 which may be measuring various parameters such as temperature, relative humidity, CO2, CO, volatile organic compounds, radon etc. The analog signal conditioning circuitry 202 conditions the raw signal from the sensor/s 201 and provides the cleaned-up signal to the rest of the system. The analog to digital converter 203 converts the conditioned signal from the sensor/s 201 to the digital format so that any processing module 30 may process the data from the sensor/s 201. The digital filter/DSP algorithm based process run in a microprocessor or microcontroller which will further clean-up the signal from the sensor/s. The sensor module 10 further has a power sub-system 205 to regulate and supply as well control the power to the sensor/s 201. The power subsystem is 205 in turn programmed and controlled by the processing module 30 which enables the system to conserve power by providing power to components on requirement basis, sleep while not in use.

Figure 1B:
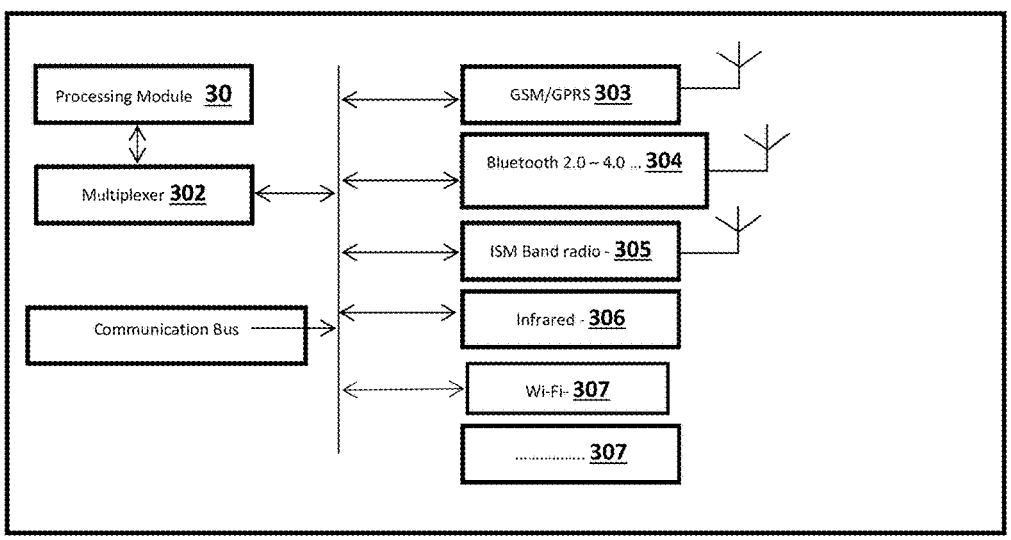
FIG. 1B illustrates the communication module, in accordance with an embodiment of the invention.

FIG. 1B illustrates the communication module 50 in accordance with an embodiment of the invention. The multiplexer 302 gets controlled by the processing module 30 to send the data to a specific communication module such as GPRS/GSM module 303 or to multitude of module such as both to GPRS as well as to the ISM band radio (Zigbee etc.). The GSM/GPRS radio 303 or some such radio is used to communicate through cellular network. The Bluetooth based radio 304 is also available. The Bluetooth based radio 304 is used to communicate with phone/phablet/tablet/laptop app or personal devices such as smart watches, bracelets. The ISM band radio/s 305 is used to communicate with similar ISM band radios in the radio vicinity of the device. The infrared based module 306 is used to communicate with similar infrared based modules or gadgets. The Wi-fi module 307 may be activated while required for communicating through the network to other devices or systems as configured. The inhaler module 20 communicates with the processing module by means of communication module 50. The communication module is capable of incorporating with any future method of communication also.

Figure 1C:
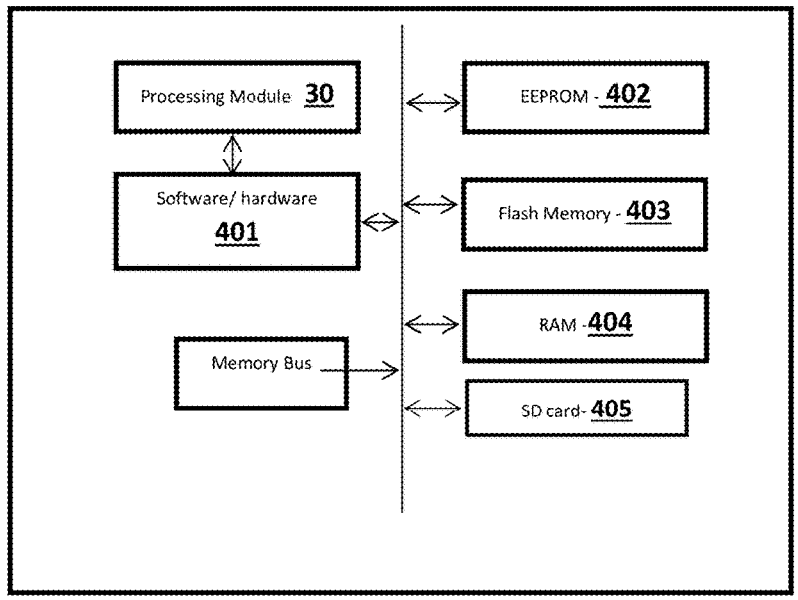
FIG. 1C describes the memory subsystem used by the data management module of the system, in accordance with an embodiment of the invention.

FIG. 1C illustrates the memory subsystem used by the data management module 60 of the system in accordance with an embodiment of the invention. The hardware/software multiplexer 401 enables the processing module 30 to store data in either of RAM/EEPROM/FLASH etc. or multiple of the said technologies simultaneously. The EEPROM 402 stores data in a non-volatile manner. The FLASH memory 403 stores data in a non-volatile manner. The RAM memory module 404 helps in storing data for processing. The system may also has a memory storage facility such as a SD card 405.

Figure 1D:
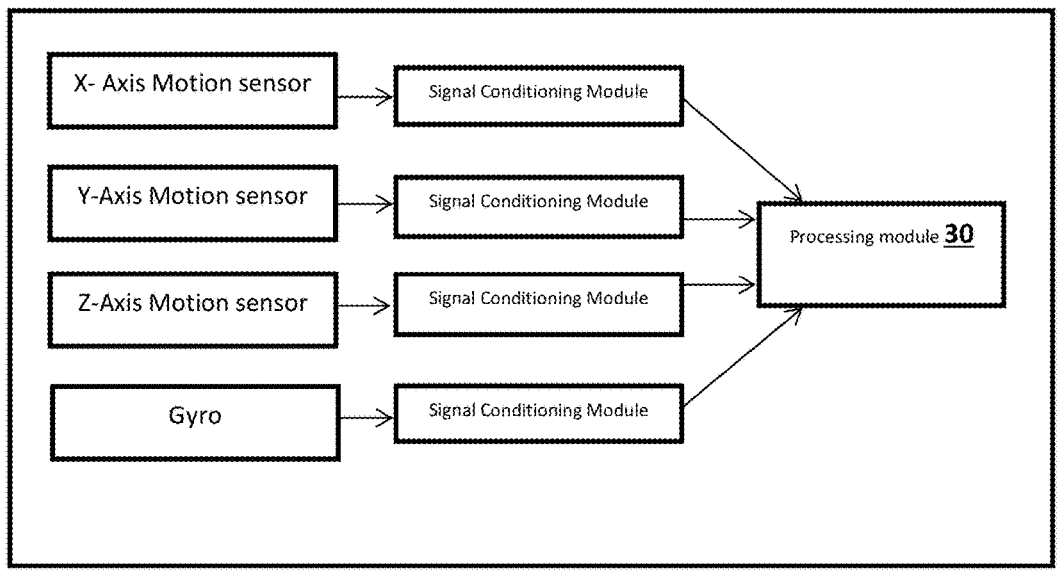
FIG. 1D shows the motion sub-system present in the data acquisition module for a motion sensor, in accordance with an embodiment of the invention.

FIG. 1D illustrates the motion sub-system present in the sensor module 10 for a motion sensor according to an embodiment of the invention. The motion sensing subsystem consists of three axes sensor/s which will sense motion of the individual in all the three axes. The output of the sensor/s will be passed through the signal conditioning circuits to eliminate any noise in the signal and the resultant signal will be passed to the processing module. In addition to the three axes motion sensor a gyro is also used to sense the motion of the individual and the output of the gyro is also processed in a similar way as described for the three axes motion sensor/s.

Figure 2:
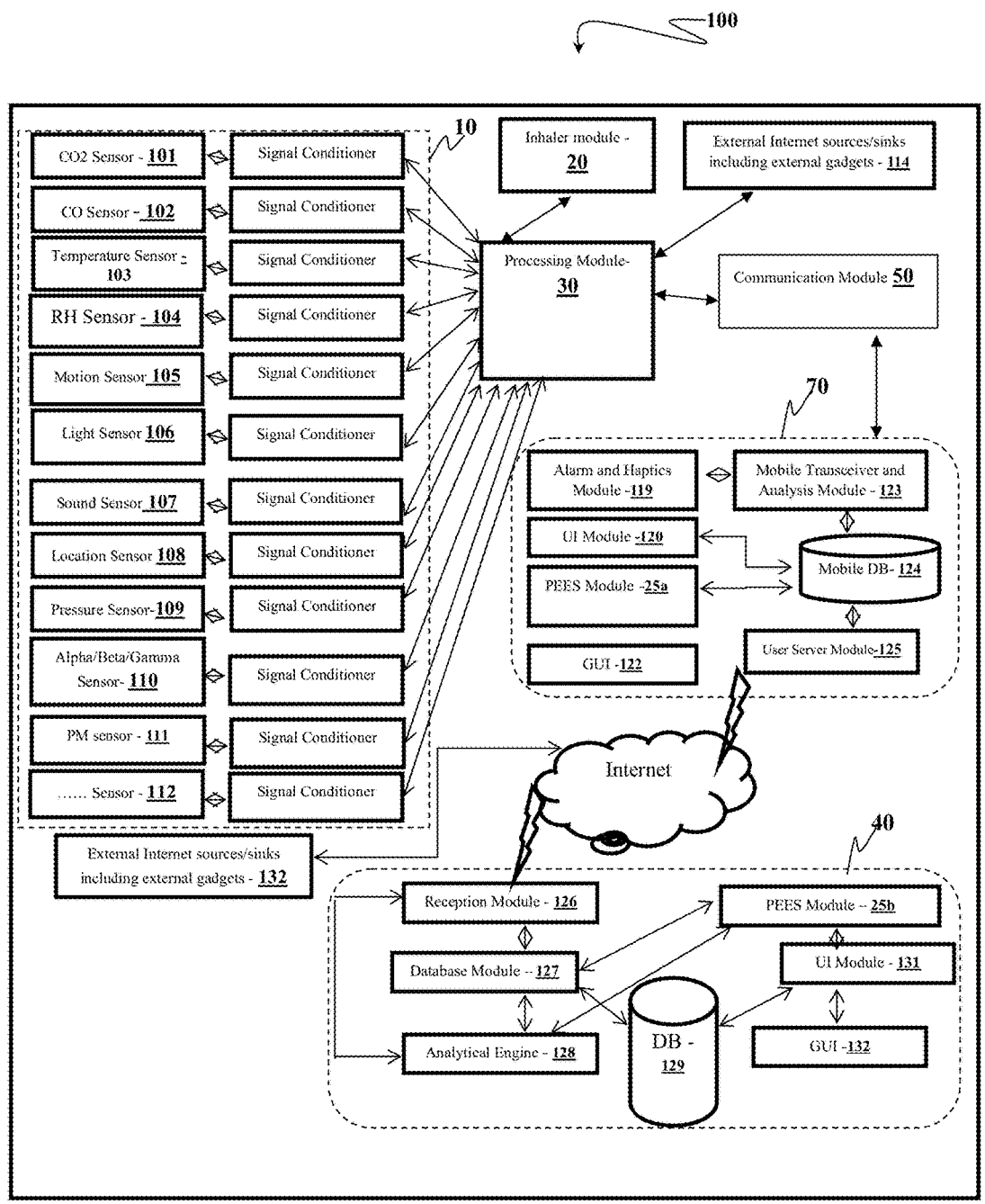
FIG. 2 illustrates the system according to an embodiment of the invention.

FIG. 2 illustrates the system according to an embodiment of the invention. The system 100 includes a sensor module 10, the sensor module includes a number of sensors to sense a variety of environmental parameters of the personal environment envelope surrounding the individual. For example the sensor module 10 has a $CO_2$ sensor 101, a CO sensor 102, a temperature sensor 103, a relative humidity sensor 104, motion sensor 105, light sensor 106, sound sensor 107, location sensor 108, pressure sensor 109, alpha/beta/gamma sensor 110 and it may have any other sensors which is capable of sensing any of the environmental features related to the individual. The sensor module 10 further does signal conditioning in order to avoid any noise in the signal. The $CO_2$ 101 senses the $CO_2$ ppm in the surrounding air of the individual and the associated signal or data may be send to the signal condition circuitry for further processing. The CO sensor 102 measures the CO ppm in the surrounding air of the individual and the associated signal or data may be sending to the signal condition circuitry for further processing. The temperature sensor 103 measures the temperature in the surrounding air of the individual and the associated signal or data may be sent to the signal condition circuitry for further processing. The relative humidity (RH) sensor 104 measures the RH in percentage in the surrounding air of the individual and the associated signal or data may be sent to the signal condition circuitry for further processing. The motion sensor/s 105 measures the movement in three axes, namely X, Y and Z and also a Gyro measures the movement of the individual and the associated signal or data will be sent to the signal condition circuitry for further processing. The light sensor 106 measures the radiation in the visible and invisible spectrum and sends the associated data for further processing, where the output of the said processing will determine whether the said radiation is harmful to the individual or not based on agreed threshold values. The sound sensor 107 measures the sound in SPL in the surroundings of the individual and gets later processed and the output of the said processing determines whether the SPL is harmful to the individual or not based on agreed threshold values. The location sensor 108 measures the location of the individual. This may be based on technologies such as GPS/GSM based location technologies etc. The location sensor may also provide the altitude of the position of the user from mean sea level (MSL). The calculation of the wind direction can be either taken from wind direction sensor or from the web. The location of the individual can be calculated either from GPS or through GSM GPRS or through IP location etc. The pressure sensor 109 sends the data regarding the ambient/barometric pressure to the processing module 30 through a signal conditioning circuitry. Through the data from the pressure sensor, the system will determine the altitude of the location of the individual from the mean sea level (MSL). The alpha/beta/gamma wave sensor 110 senses the neurological activity of the individual and the data will be sent to the microprocessor. The microprocessor runs an algorithm/s to determine the mental state of the individual based on the waves generated by the individual. Particulate matter (PM) sensor 111 provides the details of count and distribution by size of particulate matter in microns from the air conveyed through it in the device to the micro processor. Any other sensor 112 is to illustrate that the system is capable of incorporating any sensor to capture any other environmental data surrounding the individual or the biological or physiological condition of the individual and sends such data to the processing module. The processing module 30 includes the microprocessor for further processing. The processing module also receives data from the inhaler module 20. The system also receives data from external sources. The external sources might be other gadgets or sensors which might provide information to the system. The external sinks might be gadgets/appliances which might use the data generated by the device or the external sinks might be commanded based on certain thresholds by the device. Ambient/Outside air properties available through a plurality of sources such as external sources or other readily readable or processed to compute ambient air properties. Based on the ambient/outside air properties and computation of the indoor properties based on the data collected through the sensors through an algorithm, a reference set of parameters would be available for adaptive comfort setting of the air conditioning devices.

The inhaler module 20 tracks when and where the user has taken medication and also includes a dosage counter. The dosage counter counts the number of dosage available in the inhaler. The sensors for counting the dosage are fixed on the holster of the inhaler. Further the inhaler module 20 stores the data regarding the expiry of the medicine, batch of the medicine and so on. The system further includes an inhaler setting module to set the timing and dosage in accordance with the inhalation routine of the user.

The system also has a processing module 30 to collect data from multiple numbers of environmental sensors regarding ambient environmental conditions with reference to a geographical location of the individual. The processing module 30 also collects data from plurality of external sources regarding ambient environmental conditions with reference to the geographical location of the individual and the personal environmental envelope. The processing module 30 further dynamically processes the information from the inhaler module 20 including the time and location from where the user has taken medication. The processing module 30 processes the sensor data so as to identify the environmental parameters that may have caused the need for medication especially if the dosage is not according to routine medication. If the processing module 30 identifies a deviation from the preferred settings in the environment or in the usage of medication then the processing module 30 generates alerts to the desired users. The desired user includes the one who takes the medication and their care takers including medical professionals. The alert generated by the processing module includes alerts when the user misses routine dosage of medication. The alerts are transmitted as at least one of a audio visual messages. The system also capable of learning from the user's history of usage of inhaler. The processing module 30 further generates alert when the system identifies a hostile condition in an impending route preferred by the individual. The processing module 30 with the help of communication module 50 gets access to a multitude of communication technologies to transmit data to the user's smart devices such as smart phones, tablets, phablets, smart watches, bracelets etc. as well as to the internet. According to an embodiment a buzzer or haptics/vibration actuator is coupled to the processing module to alert the user about any hazardous conditions based on thresholds which the user has created for himself/herself. The user may be any registered user to know the individual's data or alerts or the individual itself. According to an embodiment the output or the alert from the processing module 30 may be given through LED/LCD/projector. The output might be the parameters calculated by the device as well the alarms raised by the device. In another embodiment, the output may be through a single or a set of LED's or a multi-colored LED which will change its color based on certain inputs from the processing module. The color of the LED will indicate whether the environment around the user is preferred or safe or hazardous. The colors of the LED can be configured individually by the user According to an embodiment of the invention the memory subsystem of the server may present in the system itself. The memory sub-system comprises of RAM, non-volatile RAM, Flash memory, EEPROM etc. which are used for storing and retrieving data based on the availability of the communication medium as well for the purpose of proper computation of the algorithms. The communication module 50 gets data from the processing module 30 and transmits the information to the relevant locations. The communication module 50 uses numerous technologies such as GSM/GPRS, ISM band radios, Bluetooth versions, Wi-Fi, Infrared communication using various protocols etc. The communication module 50 is further capable of receiving and transmitting data between various modules of the system as well as to the user devices. The communication module 50 is capable of transmitting the sensor data from the sensor module 10 and inhalation details and medication details from the inhaler module 20 to the user's computing devices such as mobile phone/phablet/tablet application which in turn may be sent to the backend server. In certain scenario the processing module 30 may present in the user's computing devices. This is possible when the user's device has a software application which processes the data from the sensor module as well as personal environment setting module. The communication module 50 is also responsible for transmitting data to the server module 40 for storing and for future usage.

According to an embodiment of the invention the system 100 as shown in FIG. 2 further has a mobile or user device module 70 configured to receive data from the processing module 30 where the alarm and haptics module 119 in the user device raises the alarms or haptics (vibrations) in the user device. The user device includes any computing device which is capable of communicating with the system such as mobile phone, phablet, tablet or personal computer. The user device module 70 further has a user interface (UI) module 120 which controls the user interface. The user interface module 120 is tailored according to various operating systems which is available. The personal environment envelop setting module (PEES module) 25a in the user device enables the user to configure his/her preferred settings such as $CO_2$/RH/Temperature/Particulate Matter levels etc. Those preferred settings are transferred to the device as well to the backend server through the communication module 50 so that the configuration set by the individual is available everywhere in the system. The GUI module 122 takes inputs from the user interface module and renders the graphics on the mobile phone/phablet/tablet based on the OS, screen size, resolution etc. The mobile transceiver and analysis module 123 is in the phone/phablet/tablet application analyses the data got from the processing module. The analysis is based on the configuration data set in the personal environment envelop setting module 25a. The user device module 70 further has a database module 124 in the user device which stores the data from the processing module as well the confirmation data. This module stores historical data as well as data which were not sent over to the server module 40. The personal environment envelop setting module 25a decides whether the data needs to be stored locally or not. The user server module 125 of the user device module 70 sends the data or receive the data as well the configuration information from or to the Internet. The server module 125 also responsible to pull or push data to the external gadgets and which might be designed to receive or send such data. The system is designed to receive information from other publically available information typically provided by Government agencies and other agencies on weather conditions, pollen levels and other such data which in turn would be received through an application programming interface (API) for use by the processing module 30 or server module 40 or by both of theses modules.

The server module 40 does the data management at the bank end side. The reception module 126 is a backend server which has a multithreaded application which receives data from millions of individuals. The plurality of data from a large set of individuals with various preferences based on their conditions, illness if any, chronic ailments if any, is most useful for predictive and prognostic advisory that will enable value added services as well as provide deep insights for public health and epidemiology. The database module 60a receives the data from reception module 126 and stores the data in a RDBMS or such similar technology. The server module may be further capable of doing analytics on the data. Thus the stored data is used for analysis as well for generating info-graphics and also for future use. The analysis engine 128 in the server module 40 which analysis the data based on personal environment configuration settings and may send warnings or alerts to the user. The warnings might be in the form of SMS messages or missed calls or voice calls with configured messages. The server in the cloud also has database that has information procured from other sources about location, weather data, pollen, flora, fauna and other such environmental data, physical, chemical and biological properties of air, algorithms and heuristic machine learning capabilities to receive, analyze, process data and information received with an ability to communicate to an individual or group or a community.

There is a non-volatile database 129 based on RDBMS or some such technology which may be used to store the data as well the results from the analysis from an analytical engine 128. The non-volatile database 129 stores the user credentials for each user which is used by the user to enter the web-site. The server module 40 further has a personal environment envelop setting module (PEES module) 25*b* to take inputs from the user, either from GUI 132 on the Internet or from the phone/phablet/tablet app through the GPRS or some such communication technology. The server module 40 uses algorithms for preferred health setting recommendations for different illnesses. The server module 40 also has provisions for incorporating algorithms based on contemporary findings on adaptive control for thermal comfort. The server module 40 would comprise of content generation through contemporary medical research and published data as well as releases from institutions such as FDA or EPA regarding recommended indoor environment, thus preferred personal cloud or micro environment settings for the user should there be any specific illness or ailment. With this as the reference, as the user records get updated, the preferred settings would correspond to the acclimatized micro environment/personal cloud. An algorithm to learn out of such acclimatized settings would in effect become the preferred personal settings. Thus server module along with the data management module accumulates data of all the users regarding preferred settings, ambient weather conditions and contemporary findings on thermal comfort, adaptive comfort settings and also provides data for personal settings. The individual record mapped with the illness along with the micro environment that the user experience would provide most useful data for analytics for epidemiology.

Figure 3:
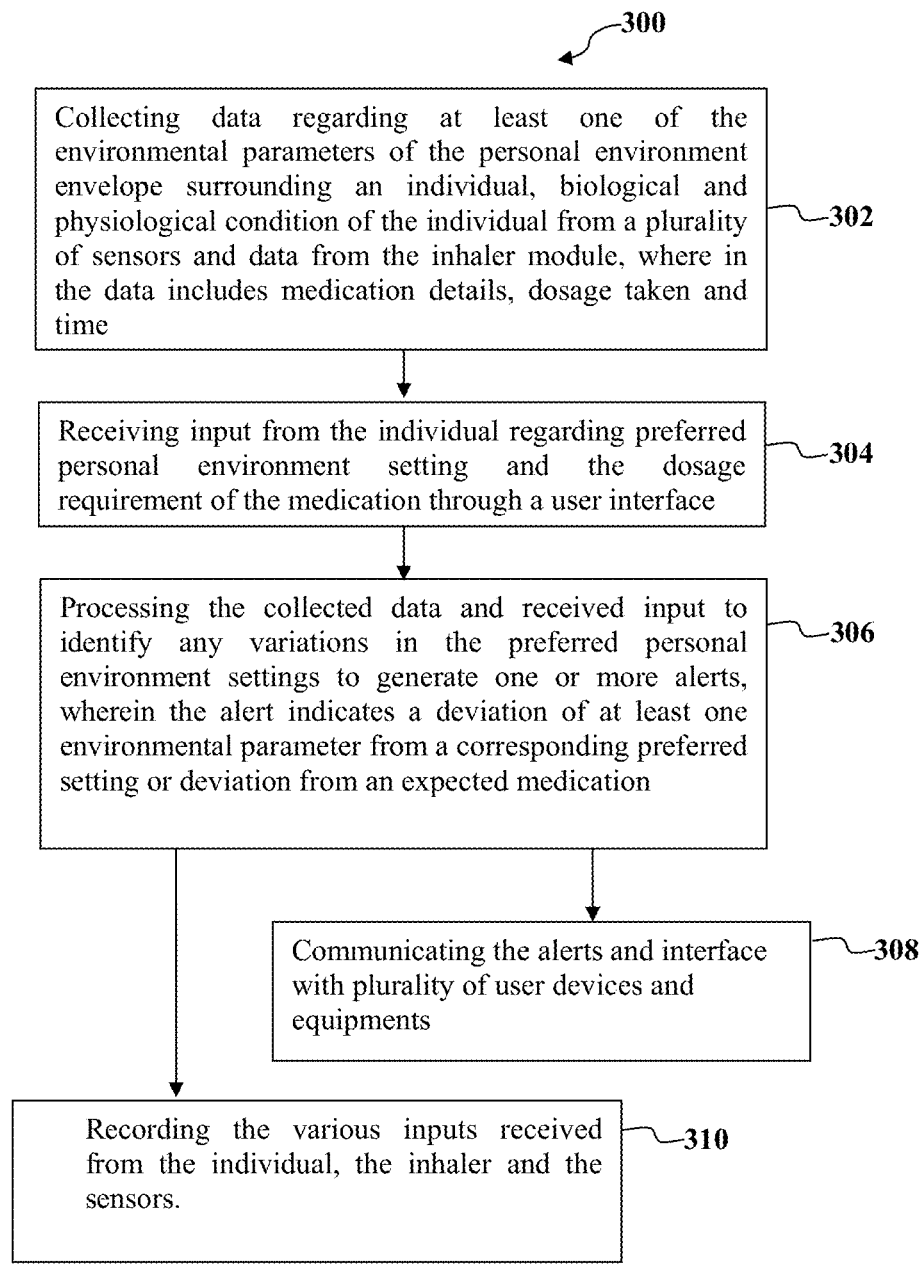
FIG. 3 illustrates the flowchart of the method, in accordance with an embodiment of the invention.

According to an embodiment, the invention discloses method for recording personal environment and to enable preferred personal indoor environment. FIG. 3 illustrates the flow of the method. The method includes step 302 of collecting data regarding environmental parameters of the personal environment envelope surrounding an individual and biological and physiological conditions of the individual from a plurality of sensors. The method also includes the step 304 of collecting data from the inhaler module, where in the data includes medication details, dosage taken and time. The method includes the step 306 of receiving input from the individual regarding preferred personal environment setting and the dosage requirement of the medication through a user interface. Here the individual provides the details about the dosage of the medicine along with the time at which he has to take the medicine. The user interface may be a web page accessed through either smart phone or any other electronic devices. The user interface may be a part of a smart phone application, through which the user may access the various settings and configurations. The method also includes the step 308 of processing the collected data and received input to identify any variations in the preferred personal environment settings to generate one or more alerts, wherein the alert indicates a deviation of at least one environmental parameter from a corresponding preferred setting or deviation from an expected medication or an hostile condition in an impending route. The alert may also be about the potential need for the medication in an impending route the individual prefers.

According to another embodiment, the method further includes the step 310 of communicating the alerts and interface with plurality of user devices and equipments. The step of collecting data further has data of the individual's biological and physiological conditions from the sensors implanted in the body or worn on the body. The method further includes the step of recording the various inputs received from the individual, the inhaler and the sensors. The method also includes the step of mapping the medication details to the location and time at which the medication is taken.

The various inputs includes the dosage details of medication and the timing of the dosage, the preferred personal environment, the personal environment of the individual along with inhaled air properties, the usage of inhaler by the individual and so on. These information from the individuals enables the system to perform various analytics on the data recorded from various individuals to understand more about the pollution and occurrence of asthmatic attack and the relationship between these.

According to an embodiment, the invention provides the mapping of medication history with respect to person's dynamic. The invention helps in tracking the routes or areas in which the person travels and map the usage of medication, time and location at which the medication has been taken. The details of medication may be marked in the route. This enables one to understand about the usage of medication and the impact of location on the usage of medication. The system may further generate alerts depending on the mapping of medication history with respect to person's dynamic, when the person is again in a similar route, which has the same environment as that of the previous route that caused the person to have medication. It is also possible to foreseen such situation and generate a warning or alert. If the system has the details of any other person travelling through a particular region needed medication, then system may forecast about possible pollution in a proposed route of the user. The system may further generate alerts or warnings about potential need for medication in an impending route to a particular location by collecting environmental parameters from various external sources of a particular location or a route to the particular location.

According to an embodiment, the system has various user interfaces that communicate with the inhaler holster, personal device and server in the cloud, with ability for two way communication between these systems enabling an integrated intelligent inhaler holster system. The user interface may be a part of the user devices such as smartphone, phablet or tablet or any such smart devices.

Figure 4:
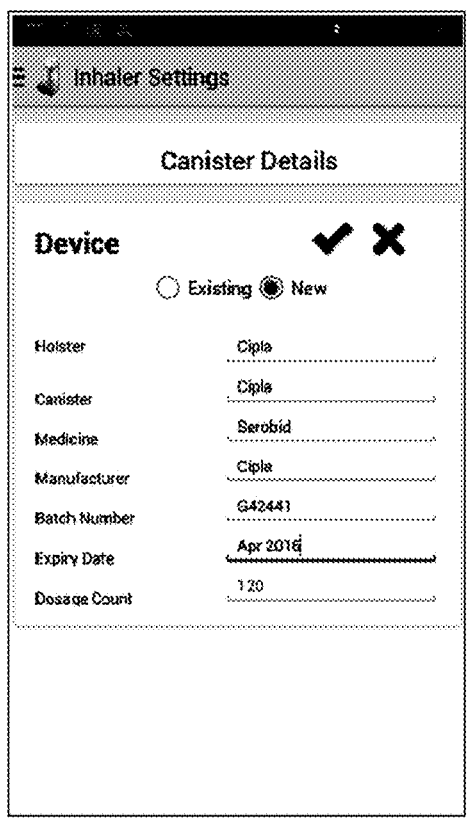
FIGS. 4-9 illustrate the various user interfaces, in accordance with an embodiment of the invention.
Figure 5:
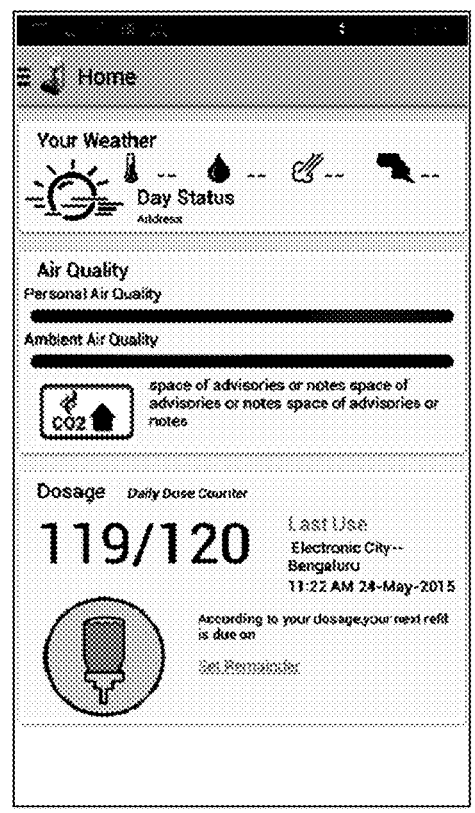

FIGS. 4-9 illustrate the various user interfaces, in accordance with an embodiment of the invention. These drawings are enclosed to this description, which are intended for purposes of illustration only and not in a limiting sense. FIG. 4 illustrates the user interface displaying the inhaler details or canister details. This interface helps the individual to know about the medication details including name of the medicine, manufacturer, batch number, expiry date and the dosage count. FIG. 5 illustrates the primary interface which is the home page. The home page gives the details about the present whether, air quality including both personal air quality based on the personal environment and the ambient air quality though a simple color schema say Green/Amber/Red depicting good, acceptable and hostile conditions for the patient. If the system identifies or generates any advisory then such advisories are displayed in this page. The home page also includes the details of the dosage counter including the details about home many dosages remaining out of the total dosages and also about the last usage of the medication. This page may also give details about the expected time to refill the canister according to the usage of the individual. The user may be able to set remainders about the next dosage.

Figure 6:
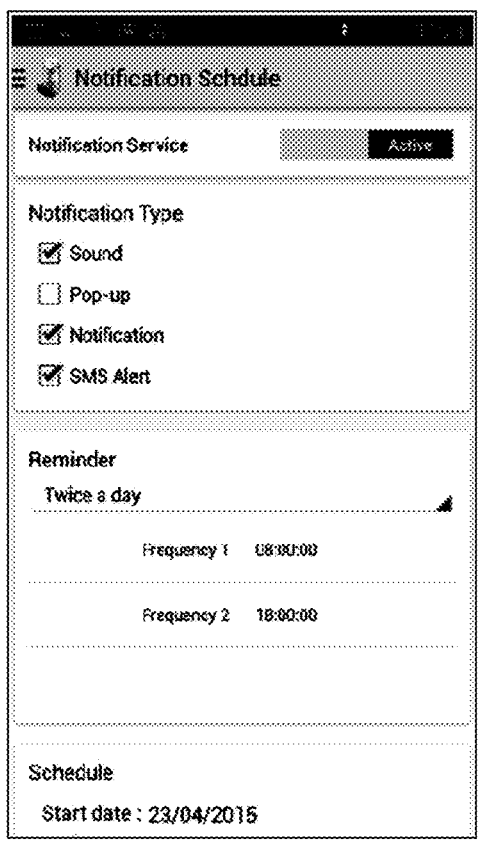
Figure 7:
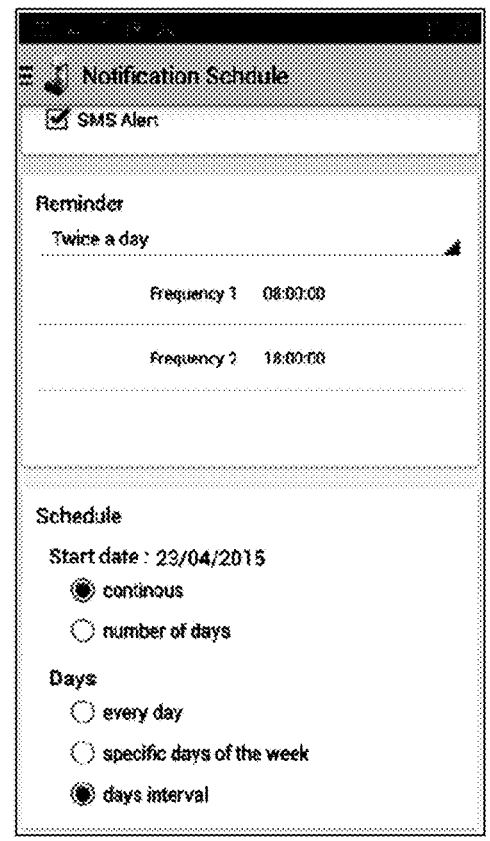

FIGS. 6 and 7 illustrate the notification setting pages in accordance with an embodiment of the invention. FIG. 6 illustrate a notification setting page to activate the notifications. The notifications may be of numerous types such as sound, pop-up, notification or sms alert. Through this notification page users or individuals may set the frequency in which they want to receive alerts. Users may also select when they want the schedule to start. If the user has requested for sms alert then the user is provided an option to give settings for sms alert. The user may select the schedule for the alerts continuous or on specific number of days in a week.

Figure 8:
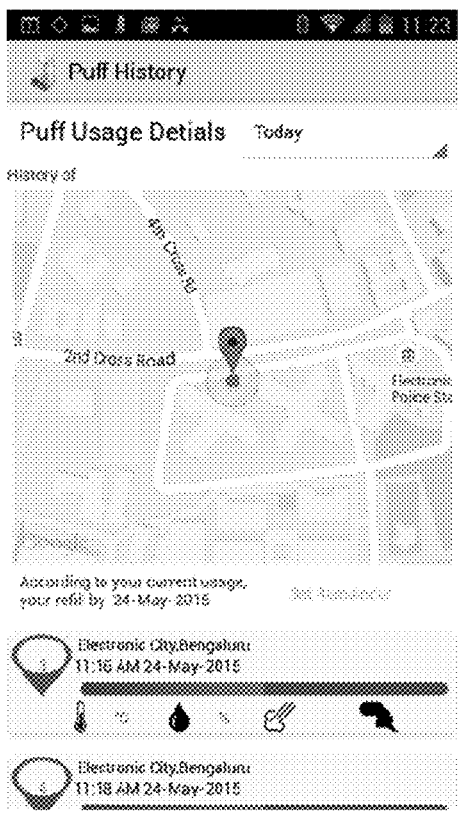
Figure 9:
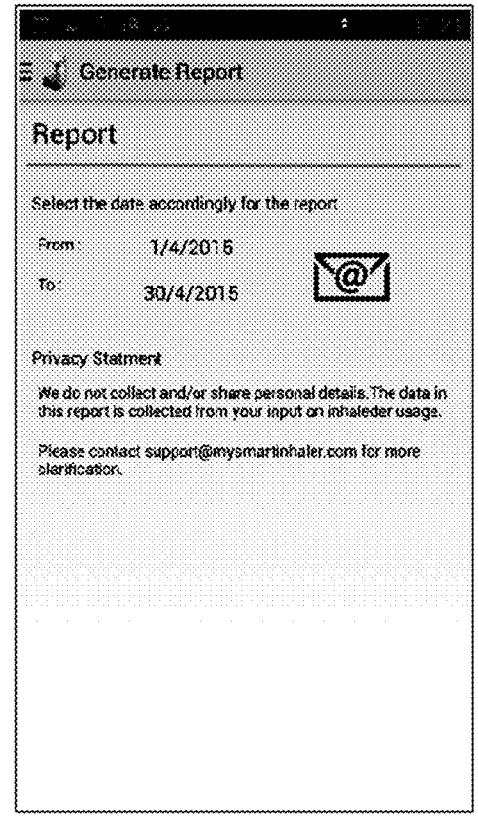

FIG. 8 illustrates the puff usage details or puff history in accordance with an embodiment of the invention. The puff usage history is shown as a map illustrating the places the individual has visited and also the instance at which he has taken the puff. This enables the individual to know how the journey through certain route results in more frequent puffs because of pollution. FIG. 9 illustrates the report generation interface in accordance with an embodiment of the invention. Here the user may request for a report on history of the usage of puff in a particular period of time. The report may be send to the individual as an email.

Thus system and method disclosed would capture the micro environment/personal cloud of the air that the individual would seek, to alert the user on missed dosage and also predictive and prognostic diagnostics for the user. The invention provides reminder as audio alerts & visual alerts on dosage to be taken. The present invention further helps the user to be conscious of locations of frequent inhalations and also to supervise the asthmatic patients. The present invention may warn patients in advance about vulnerability of places. The present invention continuously record the various environmental parameters both around an individual (effectively the inhaled air), as well as the outside weather properties along with location and time, thus mapping the entire context of an 'individual-time-inhaled air properties-outside air properties' along with details pertaining to medication, and enabling alerts or warning regarding vulnerability of a user to a location, missed dosage of medication, through a user interface, store such data in the cloud, to provide predictive and prognostic diagnostics through various methods such as SMS, email to the health care person and so on.

It is to be understood that although the invention has been described above in terms of particular embodiments, the foregoing embodiments are provided as illustrative only, and do not limit or define the scope of the invention. Various other embodiments, including but not limited to the following, are also within the scope of the claims. For example, elements and components described herein may be further divided into additional components or joined together to form fewer components for performing the same functions.

Any of the functions disclosed herein may be implemented using means for performing those functions. Such means include, but are not limited to, any of the components disclosed herein, such as the computer-related components described below.

The techniques described above may be implemented, for example, in hardware, one or more computer programs tangibly stored on one or more computer-readable media, firmware, or any combination thereof. The techniques described above may be implemented in one or more computer programs executing on (or executable by) a programmable computer including any combination of any number of the following: a processor, a storage medium readable and/or writable by the processor (including, for example, volatile and non-volatile memory and/or storage elements), an input device, and an output device. Program code may be applied to input entered using the input device to perform the functions described and to generate output using the output device.

Embodiments of the present invention include features which are only possible and/or feasible to implement with the use of one or more computers, computer processors, and/or other elements of a computer system. Such features are either impossible or impractical to implement mentally and/or manually.

Any claims herein which affirmatively require a computer, a processor, a memory, or similar computer-related elements, are intended to require such elements, and should not be interpreted as if such elements are not present in or required by such claims. Such claims are not intended, and should not be interpreted, to cover methods and/or systems which lack the recited computer-related elements. For example, any method claim herein which recites that the claimed method is performed by a computer, a processor, a memory, and/or similar computer-related element, is intended to, and should only be interpreted to, encompass methods which are performed by the recited computer-related element(s). Such a method claim should not be interpreted, for example, to encompass a method that is performed mentally or by hand (e.g., using pencil and paper). Similarly, any product claim herein which recites that the claimed product includes a computer, a processor, a memory, and/or similar computer-related element, is intended to, and should only be interpreted to, encompass products which include the recited computer-related element(s). Such a product claim should not be interpreted, for example, to encompass a product that does not include the recited computer-related element(s).

Each computer program within the scope of the claims below may be implemented in any programming language, such as assembly language, machine language, a high-level procedural programming language, or an object-oriented programming language. The programming language may, for example, be a compiled or interpreted programming language.

Each such computer program may be implemented in a computer program product tangibly embodied in a machine-readable storage device for execution by a computer processor. Method steps of the invention may be performed by one or more computer processors executing a program tangibly embodied on a computer-readable medium to perform functions of the invention by operating on input and generating output. Suitable processors include, by way of example, both general and special purpose microprocessors. Generally, the processor receives (reads) instructions and data from a memory (such as a read-only memory and/or a random access memory) and writes (stores) instructions and data to the memory. Storage devices suitable for tangibly embodying computer program instructions and data include, for example, all forms of non-volatile memory, such as semiconductor memory devices, including EPROM, EEPROM, and flash memory devices; magnetic disks such as internal hard disks and removable disks; magneto-optical disks; and CD-ROMs. Any of the foregoing may be supplemented by, or incorporated in, specially-designed ASICs (application-specific integrated circuits) or FPGAs (Field-Programmable Gate Arrays). A computer can generally also receive (read) programs and data from, and write (store) programs and data to, a non-transitory computer-readable storage medium such as an internal disk (not shown) or a removable disk. These elements will also be found in a conventional desktop or workstation computer as well as other computers suitable for executing computer programs implementing the methods described herein, which may be used in conjunction with any digital print engine or marking engine, display monitor, or other raster output device capable of producing color or gray scale pixels on paper, film, display screen, or other output medium.

Any data disclosed herein may be implemented, for example, in one or more data structures tangibly stored on a non-transitory computer-readable medium. Embodiments of the invention may store such data in such data structure(s) and read such data from such data structure(s).

I claim:

1. An intelligent inhaler holster system to sense, track properties of inhaled air and medication of an individual, the system comprises:
   a. a sensor module comprising at least one of a plurality of environmental sensors configured to sense a plurality of environmental parameters of a personal environment envelope surrounding the individual and a plurality of biological sensors to sense a plurality of biological and physiological conditions of the individual, wherein the sensors continuously sense the plurality of environmental parameters to track the properties of inhaled air;
   b. an inhaler module comprising a dosage counter, wherein the dosage counter counts the number of dosages available in the inhaler by using the dosage count data received from at least one sensor mounted on the inhaler for counting the number of dosages available in the inhaler, wherein the inhaler module tracks the medication taken by the user and details of the medication;
   c. a personal environment envelop setting module configured:
      i. to define preferred settings based on input from the individual through a user interface, wherein the input from the individual includes information not limited to the environmental preference, medication details;
      ii. to machine learn individual's preference of the personal environmental envelope and dosage of the medication with respect to the inhaled air; and
      iii. to automatically generate the preferred settings for the individual based on the learning;
   d. a processing module configured to:
      i. collect data from plurality of environmental sensors regarding ambient environmental conditions with reference to the geographical location of the individual;
      ii. collect data from plurality of external sources regarding ambient environmental conditions with reference to the geographical location of the individual and the personal environmental envelope;
      iii. collect data from the inhaler module regarding the dosage, time at which dosage is taken;
      iv. dynamically process the preferred personal environment data vis-a-vis the ambient environmental conditions and the medication details;
      v. dynamically process at least one of the plurality of environmental parameters sensed by the plurality of environmental sensors, the sensed biological and physiological condition of the individual, the medication details from the inhaler module and the preferred settings so as to learn the environmental parameters that may have caused the need for medication from a normal routine medication and to generate one or more alerts, wherein the alert indicates a deviation of at least one environmental parameter from a corresponding preferred setting or deviation from expected medication or an hostile condition in an impending route; and
   e. a server module configured to receive, store, analyze and machine learn from data of the plurality of environmental parameters and biological and physiological condition, sensed by the environmental sensors and biological sensors from the sensor module and the preferred settings along with ambient environmental data from plurality of individuals for epidemiology study;
   wherein the system alert in hostile environments, map medication with personal dynamics, inhaled air and environment for better health.

2. The system as claimed in claim 1 further comprises a communication module to receive and transmit data between various modules and to communicate alerts and interface with plurality of user devices and environment setting equipment including at least one of the HVAC (heating ventilation and air conditioning), air conditioner, humidifier, air filtering equipments or actuators to provide preferred personal environment setting to the user.

3. The system as claimed in claim 1 wherein the personal environment envelop setting module is further configured to interact and interface with plurality of environment setting equipments to achieve the preferred setting automatically for the individual based on the learnt environmental preference or medication details.

4. The system as claimed in claim 1, wherein the inhaler module further comprises an inhaler setting module to set the timing and dosage of the inhaler medication for the individual.

5. A method for recording personal environment and to enable preferred personal indoor environment, the method comprises step of:
   a) collecting data regarding at least one of the environmental parameters of the personal environment envelope surrounding an individual, biological and physiological conditions of the individual from a plurality of sensors and data from the inhaler module, where in the data includes medication details, dosage taken and time;
   b) receiving input from the individual regarding preferred personal environment setting and the dosage requirement of the medication through a user interface; and
   c) dynamically processing the collected data and received input to identify any variations in the preferred personal environment settings so as to learn the environmental parameters that may have caused the need for medication from a normal routine medication to generate one or more alerts, wherein the alert indicates a deviation of at least one environmental parameter from a corresponding preferred setting or deviation from an expected medication or a hostile condition in an impending route.

6. The method as claimed in claim 5, wherein the method further comprises step of communicating the alerts and interface with plurality of user devices and equipments including at least one of a HVAC (heating ventilation and air conditioning), air conditioner, humidifier, air filtering equipment or an actuator to provide preferred personal environment setting to the user.

7. The method as claimed in claim 5, wherein the step of collecting data further has data of the individual's biological and physiological conditions from the wearable sensors implanted in the body or worn on the body of the individual.

8. The method as claimed in claim 5, wherein the method further comprises the step of recording the various inputs received through the user interface related to preferred environment setting from the individual, the inhaler and the sensors.

9. The method as claimed in claim 5, wherein the method further comprises step of mapping the medication details to the location and time at which the medication is taken.

* * * * *